(12) United States Patent
Isaacson et al.

(10) Patent No.: US 9,155,863 B2
(45) Date of Patent: Oct. 13, 2015

(54) MULTIPLE USE STRETCHING AND NON-PENETRATING BLOOD CONTROL VALVES

(71) Applicants: S. Ray Isaacson, Roy, UT (US); Kelly D. Christensen, Centerville, UT (US); Lawrence J. Trainer, Murray, UT (US); Weston F. Harding, Lehi, UT (US)

(72) Inventors: S. Ray Isaacson, Roy, UT (US); Kelly D. Christensen, Centerville, UT (US); Lawrence J. Trainer, Murray, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 338 days.

(21) Appl. No.: 13/644,244

(22) Filed: Oct. 3, 2012

(65) Prior Publication Data
US 2013/0165868 A1 Jun. 27, 2013

Related U.S. Application Data

(60) Provisional application No. 61/544,238, filed on Oct. 6, 2011.

(51) Int. Cl.
*A61M 25/00* (2006.01)
*F16K 7/12* (2006.01)
*A61M 39/06* (2006.01)

(52) U.S. Cl.
CPC ....... *A61M 25/0097* (2013.01); *A61M 39/0693* (2013.01); *A61M 2039/066* (2013.01); *Y10T 29/49826* (2015.01)

(58) Field of Classification Search
CPC ............... A61M 25/0012; A61M 25/0074; A61M 25/0075; A61M 2025/0076; A61M 2005/3128; A61M 2039/0081; A61M 2039/064; A61M 2039/066; A61M 2039/2426; A61M 25/0028; A61M 25/0029; A61M 25/003; A61M 2025/0079; A61M 2039/226; A61M 2039/2433; A61M 2039/246
USPC .................... 604/34, 167.02, 167.03, 167.04
See application file for complete search history.

(56) References Cited

U.S. PATENT DOCUMENTS

| 4,387,879 A | 6/1983 | Tauschinski |
| 4,449,693 A | 5/1984 | Gereg |
| 4,758,225 A | 7/1988 | Cox et al. |
| 4,773,552 A | 9/1988 | Boege et al. |

(Continued)

FOREIGN PATENT DOCUMENTS

| CA | 2 133 053 A1 | 3/1995 |
| DE | 20 2009 009 602 U1 | 12/2009 |

(Continued)

OTHER PUBLICATIONS

Elson Silva, PhD, "Respecting Hydrology Science in the Patenting System," pp. 1-7, Jan. 13, 2011.

*Primary Examiner* — Nicholas Lucchesi
*Assistant Examiner* — Justin L Zamory
(74) *Attorney, Agent, or Firm* — Jeanne Lukasavage; Craig Metcalf; Kirton McConkie

(57) ABSTRACT

The current invention relates to infusion devices, specifically to peripheral intravenous (IV) catheters. In particular, the invention relates to peripheral IV catheter assemblies having features to enable selective and reversible activation of fluid flow through the catheter assembly. Some implementations of the present invention include various configurations of septum valves having a barrier surface that is stressed to bias the barrier surface and provide a pathway through the septum valve.

20 Claims, 16 Drawing Sheets

(56) References Cited

U.S. PATENT DOCUMENTS

| | | | |
|---|---|---|---|
| 4,781,702 | A | 11/1988 | Herrli |
| 4,809,679 | A | 3/1989 | Shimonaka et al. |
| 4,842,591 | A | 6/1989 | Luther |
| 4,874,377 | A | 10/1989 | Newgard et al. |
| 4,917,668 | A | 4/1990 | Haindl |
| 4,935,010 | A | 6/1990 | Cox et al. |
| 4,950,257 | A | 8/1990 | Hibbs et al. |
| 5,041,097 | A | 8/1991 | Johnson |
| 5,053,014 | A | 10/1991 | Van Heugten |
| 5,062,836 | A | 11/1991 | Wendell |
| 5,064,416 | A | 11/1991 | Newgard et al. |
| 5,084,023 | A | 1/1992 | Lemieux |
| 5,085,645 | A | 2/1992 | Purdy et al. |
| 5,098,405 | A | 3/1992 | Peterson et al. |
| 5,108,374 | A | 4/1992 | Lemieux |
| 5,127,905 | A | 7/1992 | Lemieux |
| 5,154,703 | A | 10/1992 | Bonaldo |
| 5,156,596 | A | 10/1992 | Balbierz et al. |
| 5,176,652 | A | 1/1993 | Littrell |
| 5,234,410 | A | 8/1993 | Graham et al. |
| 5,269,771 | A | 12/1993 | Thomas et al. |
| 5,290,246 | A | 3/1994 | Yamamoto et al. |
| 5,295,658 | A * | 3/1994 | Atkinson et al. ............ 251/149.1 |
| 5,295,969 | A | 3/1994 | Fischell et al. |
| 5,330,435 | A | 7/1994 | Vaillancourt |
| 5,350,363 | A | 9/1994 | Goode et al. |
| 5,352,205 | A | 10/1994 | Dales et al. |
| 5,405,323 | A | 4/1995 | Rogers et al. |
| 5,456,675 | A | 10/1995 | Wolbring et al. |
| 5,474,544 | A | 12/1995 | Lynn |
| 5,487,728 | A | 1/1996 | Vaillancourt |
| 5,520,666 | A | 5/1996 | Choudhury et al. |
| 5,549,566 | A | 8/1996 | Elias et al. |
| 5,549,577 | A | 8/1996 | Siegel et al. |
| 5,575,769 | A | 11/1996 | Vaillancourt |
| 5,613,663 | A | 3/1997 | Schmidt et al. |
| 5,651,772 | A | 7/1997 | Arnett |
| 5,657,963 | A | 8/1997 | Hinchliffe et al. |
| 5,697,915 | A | 12/1997 | Lynn |
| 5,738,144 | A | 4/1998 | Rogers |
| 5,749,861 | A | 5/1998 | Guala et al. |
| 5,806,831 | A | 9/1998 | Paradis |
| 5,817,069 | A | 10/1998 | Arnett |
| 5,833,674 | A | 11/1998 | Turnbull et al. |
| 5,911,710 | A | 6/1999 | Barry et al. |
| 5,954,698 | A | 9/1999 | Pike |
| 5,967,490 | A | 10/1999 | Pike |
| 6,039,302 | A | 3/2000 | Cote, Sr. et al. |
| 6,077,244 | A | 6/2000 | Botich et al. |
| 6,117,108 | A | 9/2000 | Woehr et al. |
| 6,171,287 | B1 | 1/2001 | Lynn et al. |
| 6,273,869 | B1 | 8/2001 | Vaillancourt |
| 6,287,280 | B1 | 9/2001 | Lampropoulos et al. |
| 6,485,473 | B1 | 11/2002 | Lynn |
| 6,575,960 | B2 | 6/2003 | Becker et al. |
| 6,595,981 | B2 | 7/2003 | Huet |
| 6,699,221 | B2 | 3/2004 | Vaillancourt |
| 6,719,726 | B2 | 4/2004 | Meng et al. |
| 6,740,063 | B2 | 5/2004 | Lynn |
| 6,883,778 | B1 | 4/2005 | Newton et al. |
| 7,008,404 | B2 * | 3/2006 | Nakajima ..................... 604/158 |
| 7,347,839 | B2 | 3/2008 | Hiejima |
| 7,396,346 | B2 | 7/2008 | Nakajima |
| 7,470,254 | B2 | 12/2008 | Basta et al. |
| 7,736,339 | B2 | 6/2010 | Woehr et al. |
| 7,914,494 | B2 | 3/2011 | Hiejima |
| 7,938,805 | B2 * | 5/2011 | Harding et al. .......... 604/167.04 |
| 2006/0163515 | A1 | 7/2006 | Ruschke |
| 2007/0083157 | A1 | 4/2007 | Belley et al. |
| 2007/0083162 | A1 | 4/2007 | O'Reagan et al. |
| 2007/0233007 | A1 * | 10/2007 | Adams ..................... 604/168.01 |
| 2008/0039796 | A1 | 2/2008 | Nakajima |
| 2008/0108944 | A1 | 5/2008 | Woehr et al. |
| 2008/0287921 | A1 | 11/2008 | Bennett |
| 2009/0281525 | A1 * | 11/2009 | Harding et al. ................ 604/537 |
| 2009/0287154 | A1 | 11/2009 | Harding et al. |
| 2010/0204648 | A1 | 8/2010 | Stout et al. |
| 2010/0204675 | A1 | 8/2010 | Woehr et al. |
| 2010/0222746 | A1 | 9/2010 | Burkholz |
| 2011/0046570 | A1 | 2/2011 | Stout et al. |
| 2011/0160662 | A1 | 6/2011 | Stout et al. |

FOREIGN PATENT DOCUMENTS

| | | |
|---|---|---|
| EP | 0 369 314 A2 | 5/1990 |
| EP | 0 440 426 A1 | 8/1991 |
| EP | 0 968 736 A1 | 1/2000 |
| EP | 1 129 740 A2 | 9/2001 |
| EP | 1 679 043 A1 | 7/2006 |
| WO | 93/11696 | 6/1993 |
| WO | 96/41649 | 12/1996 |
| WO | 98/00195 | 1/1998 |
| WO | 99/34849 | 7/1999 |
| WO | 99/38562 | 8/1999 |
| WO | 2006/037638 A1 | 4/2006 |
| WO | 2006/059540 A1 | 6/2006 |
| WO | 2007044878 A2 | 4/2007 |
| WO | 2008/014436 A2 | 1/2008 |
| WO | 2008/052790 A2 | 5/2008 |
| WO | 2009/114833 A1 | 9/2009 |
| WO | 2010/093791 A1 | 8/2010 |
| WO | 2012/002015 A1 | 1/2012 |

* cited by examiner

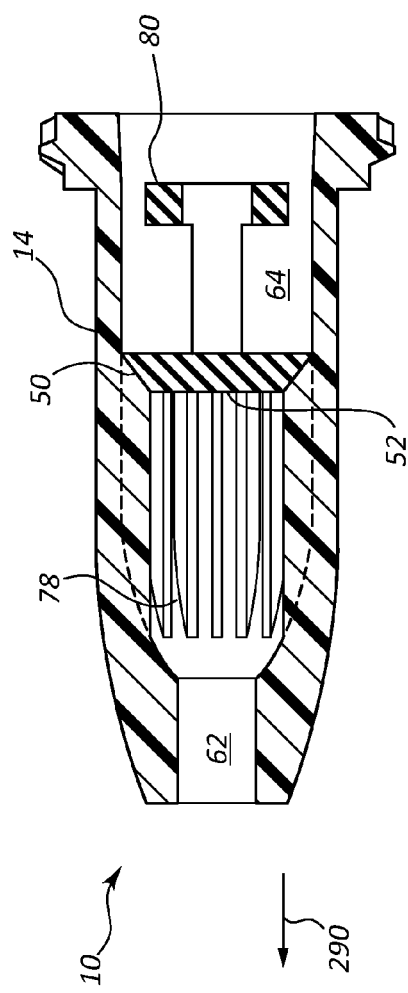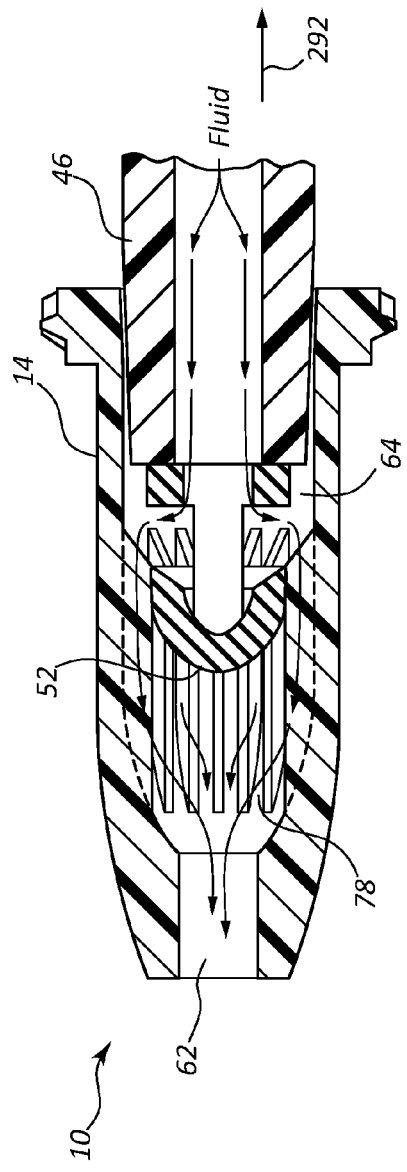
FIG. 4A
FIG. 4B

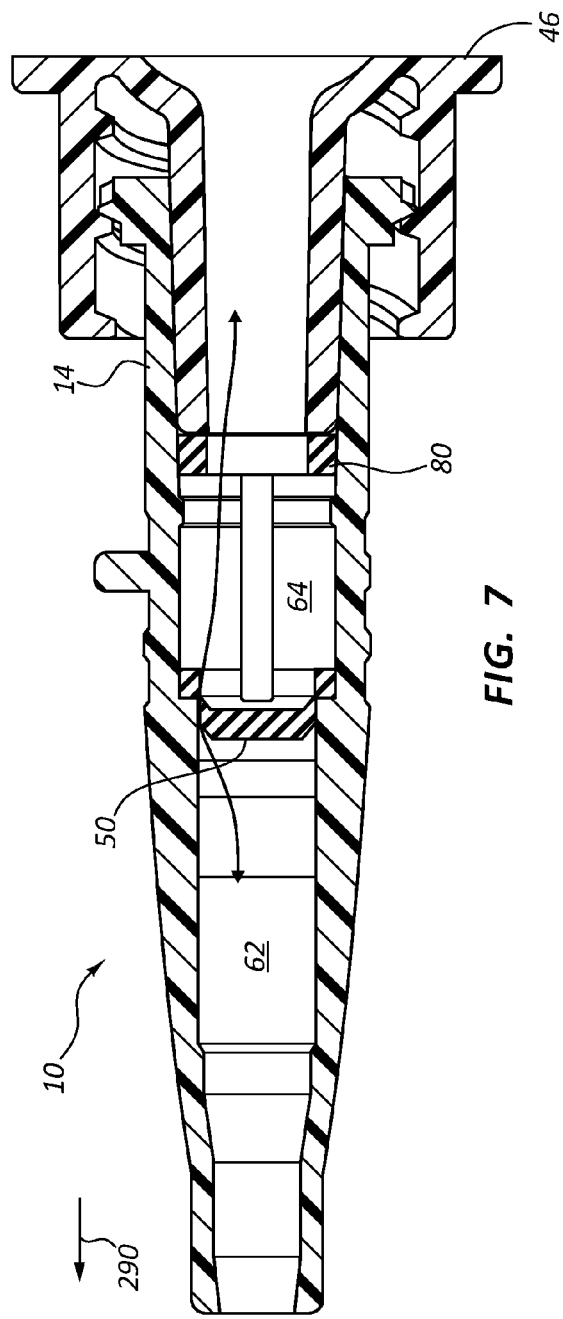
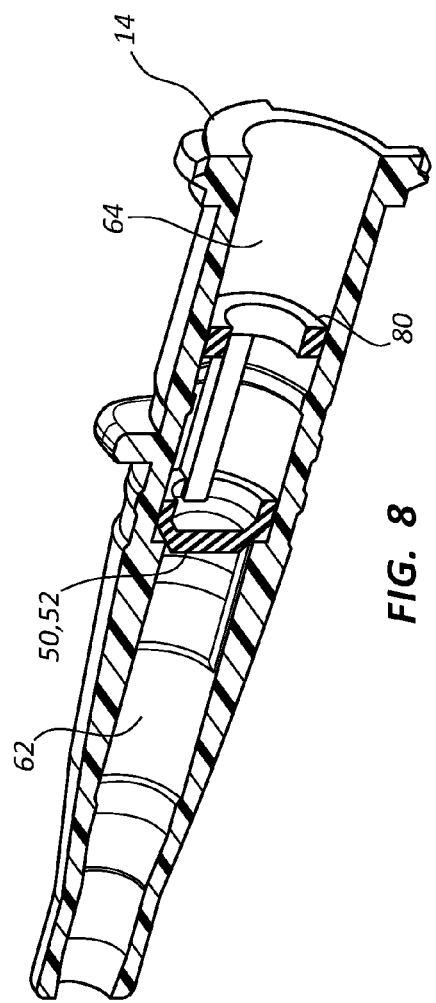

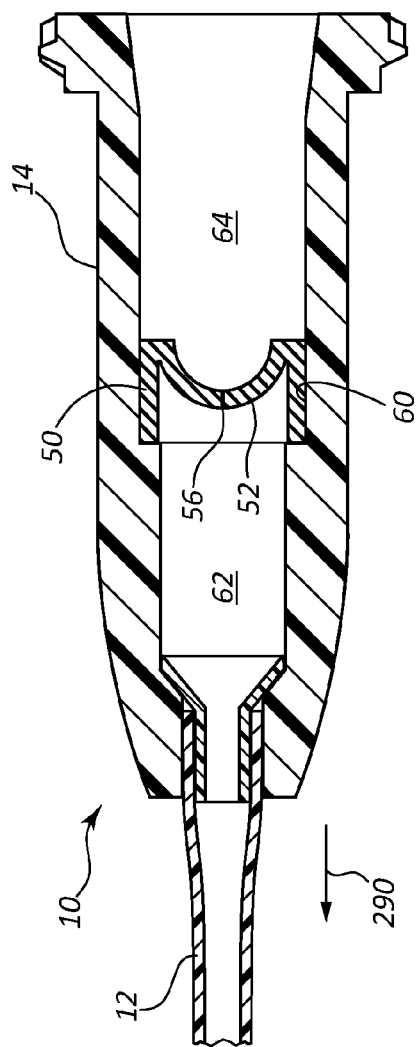
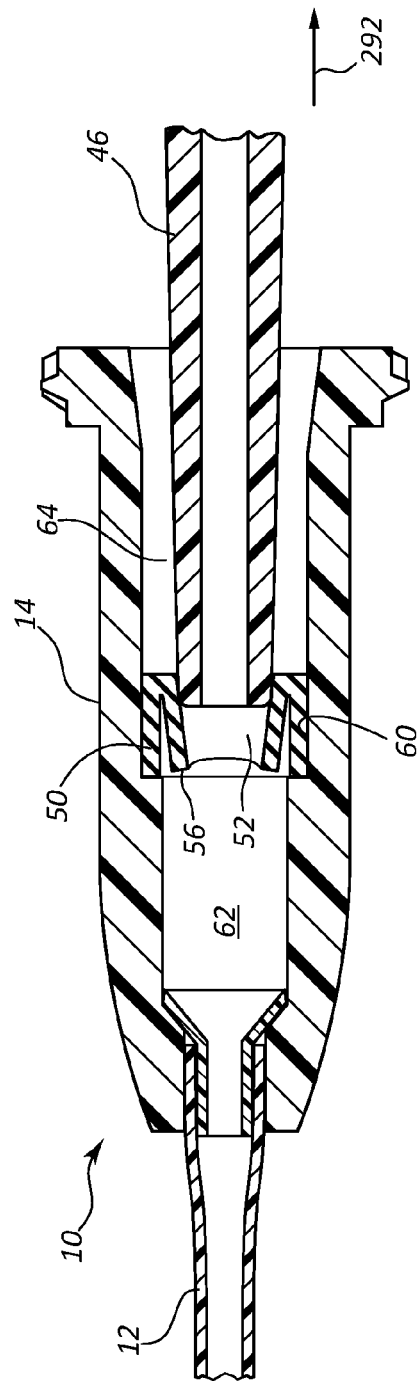
FIG. 9A
FIG. 9B

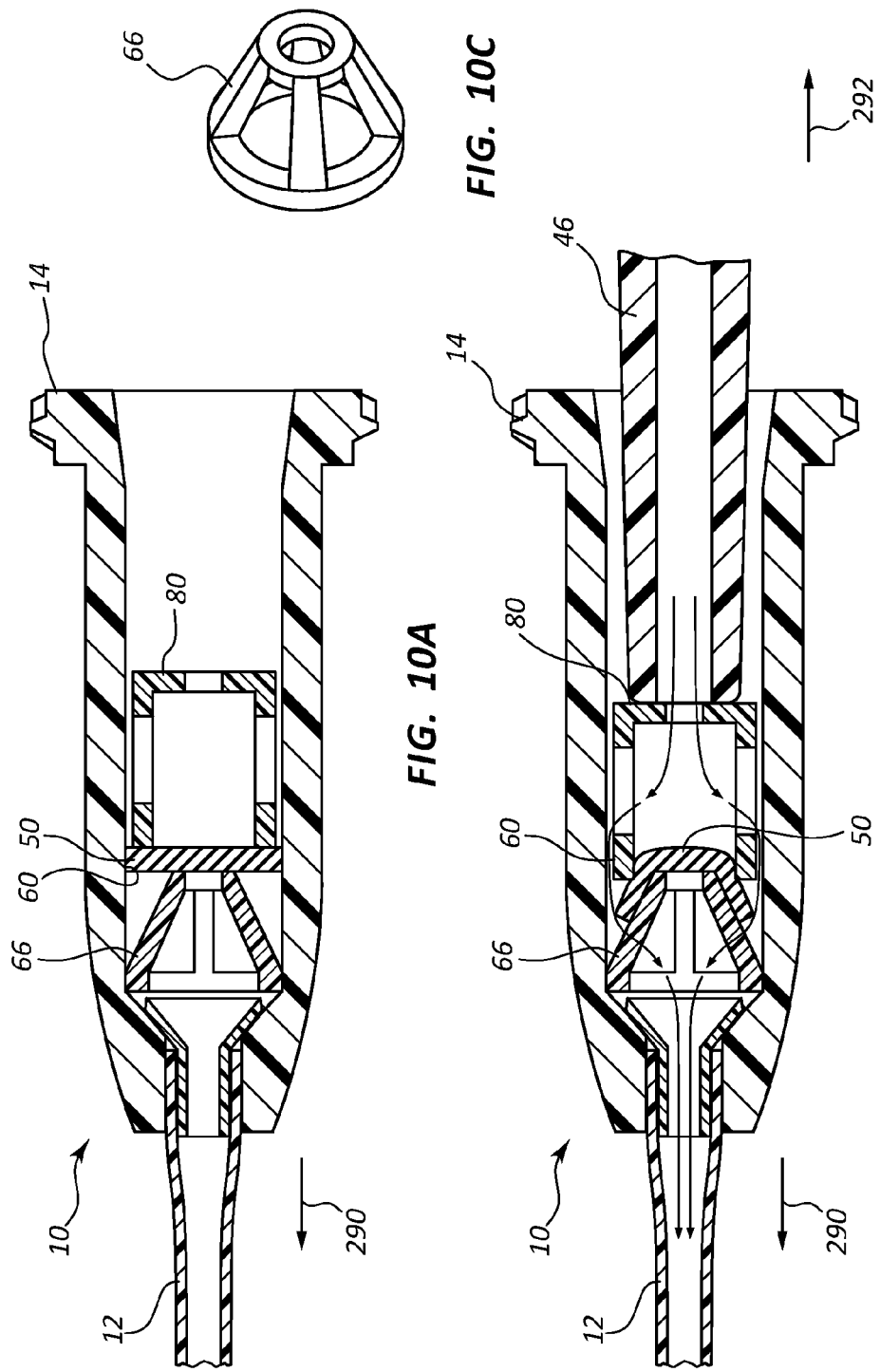

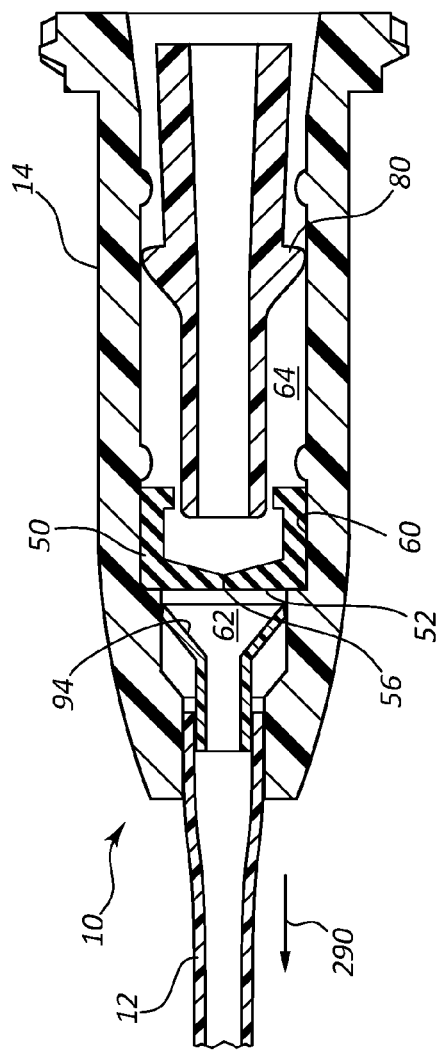
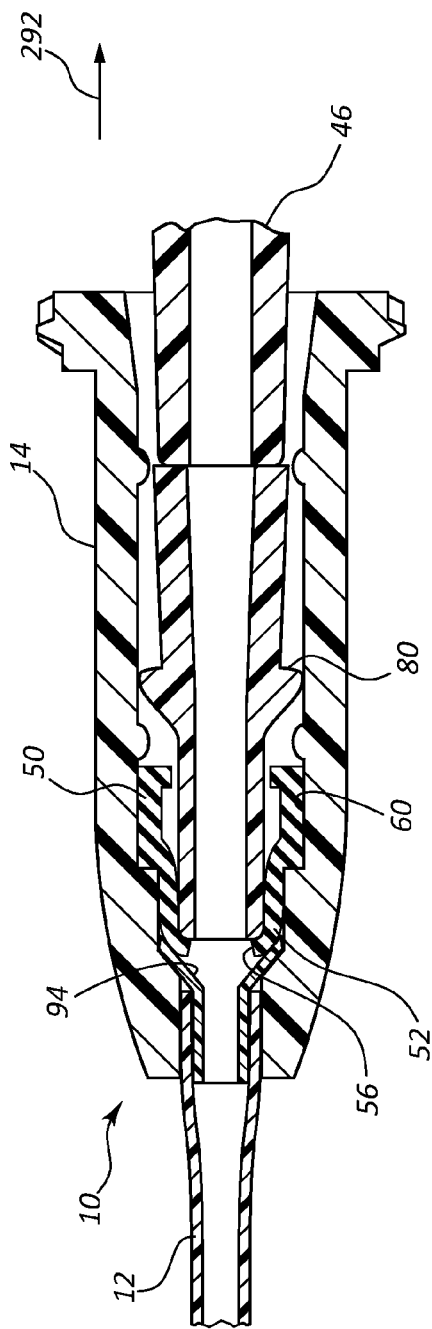
FIG. 11A
FIG. 11B

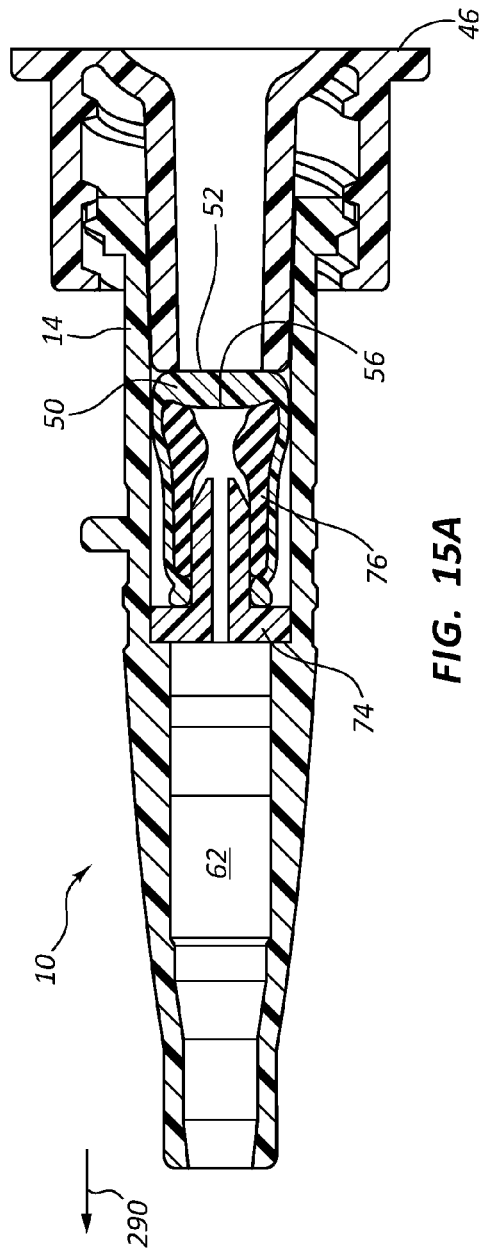
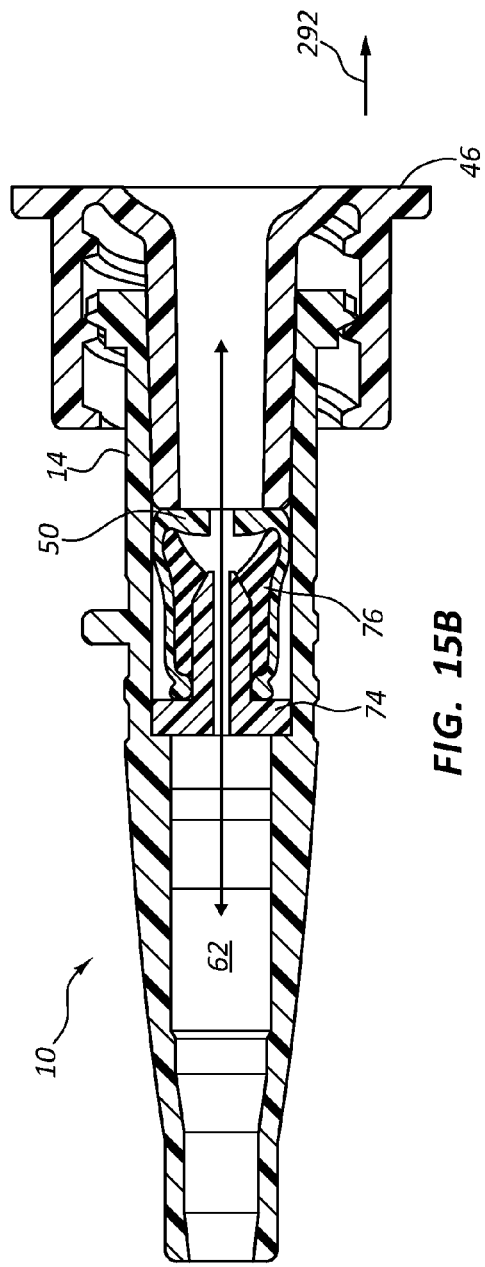
FIG. 15A
FIG. 15B

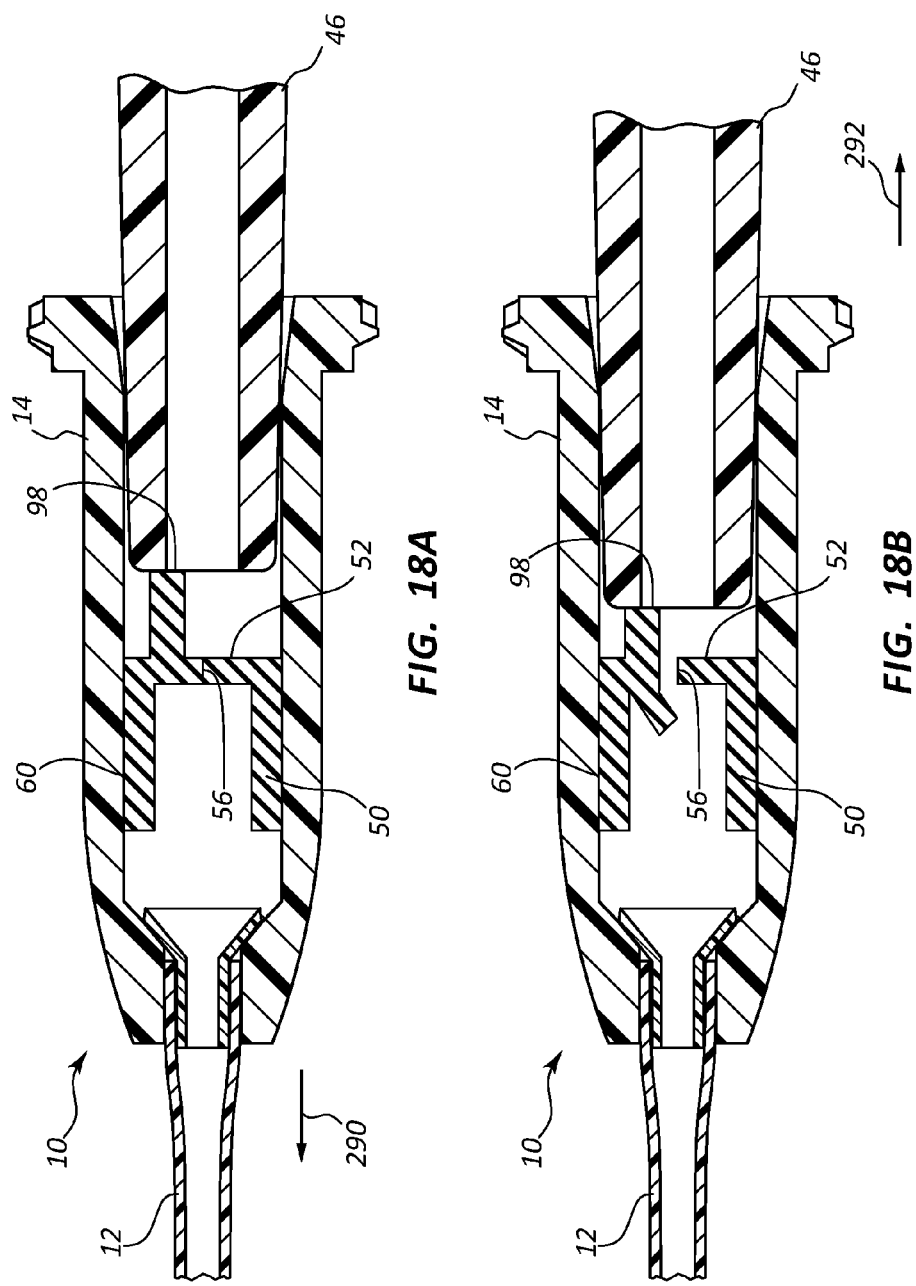

MULTIPLE USE STRETCHING AND NON-PENETRATING BLOOD CONTROL VALVES

RELATED APPLICATIONS

The present application claims priority to U.S. Provisional Patent Application Ser. No. 61/544,238, filed Oct. 6, 2011 and entitled MULTIPLE USE STRETCHING AND NON-PENETRATING BLOOD CONTROL VALVES, which is incorporated herein in its entirety.

BACKGROUND OF THE INVENTION

The current invention relates to infusion devices, specifically to peripheral intravenous (IV) catheters. In particular, the invention relates to peripheral IV catheter assemblies having features to enable selective and reversible activation of fluid flow through the catheter assembly.

Catheters are commonly used for a variety of infusion therapies. For example, catheters are used for infusing fluids, such as normal saline solution, various medicaments, and total parenteral nutrition, into a patient, withdrawing blood from a patient, or monitoring various parameters of the patient's vascular system.

Catheters and/or needles are typically coupled to a catheter adapter to enable attachment of IV tubing to the catheter. Thus, following placement of the catheter or needle into the vasculature of a patient, the catheter adapter is coupled to a fluid source via a section of IV tubing. In order to verify proper placement of the needle and/or catheter in the blood vessel, the clinician generally confirms that there is "flashback" of blood in a flashback chamber of the catheter assembly.

Once proper placement of the catheter is confirmed, the clinician must then attach the catheter adapter to a section of IV tubing, or continue to manually occlude the vein to prevent undesirable exposure to blood. The process of coupling the catheter adapter to the section of IV tubing requires the clinician to awkwardly maintain pressure on the vein of the patient while simultaneously coupling the catheter adapter and the IV tubing. A common, yet undesirable practice is to permit blood to temporarily and freely flow from the catheter adapter while the clinician locates and couples the IV tubing to the catheter adapter. Another common practice is to attach the catheter adapter to the IV tubing prior to placing the needle or catheter into the vein of the patient. While this method may prevent undesirable exposure to blood, positive pressure within the IV line may also prevent desirable flashback.

Some catheter assemblies further utilize a septum actuator and a split septum, wherein the septum actuator is mechanically advanced through a slit of the septum to provide a fluid pathway through the septum. However, once advanced through the septum, the septum actuator becomes lodged within the slit of the septum and is unable to return to its initial position. As such, the fluid pathway remains in an opened position thereby enabling uncontrolled flow of fluids through the septum.

Accordingly, there is a need in the art for a catheter assembly that permits user controlled fluid flow. Various embodiments of such a catheter assembly is disclosed herein.

BRIEF SUMMARY OF THE INVENTION

In order to overcome the limitations discussed above, the present invention relates to a flushable peripheral IV catheter assembly having features to enable selective activation of fluid flow through the catheter assembly. The catheter assembly of the present invention generally includes a catheter coupled to a catheter adapter. The catheter generally includes a metallic material, such as titanium, surgical steel or an alloy as is commonly known in the art. In some embodiments, a polymeric catheter may be used in combination with a metallic introducer needle, as is commonly known and used in the art.

In some embodiments of the present invention, a septum is positioned within a lumen of the catheter assembly to prevent or limit flow of a fluid through the catheter adapter. The septum generally includes a flexible or semi-flexible material that is compatible with exposure to blood, medicaments, and other fluids commonly encountered during infusion procedures. In some embodiments, a groove is provided on an inner surface of the catheter adapter, wherein the septum is seated within the groove. As such, the position of the septum within the catheter adapter is maintained.

In some implementations of the present invention, a closed or partially closed pathway, such as a slit or plurality of slits is further provided in a barrier surface of the septum. The pathway permits fluid to bypass the septum and flow through the catheter adapter. In some embodiments, the pathway is a slit that is closed prior to being opened or activated by a probe or septum actuator positioned within the lumen of the catheter adapter. Prior to being opened or activated, the slit prevents passage of fluid through the catheter adapter. Thus, in some embodiments a plurality of air vent channels are interposed between the septum and the groove to permit air flow through the catheter adapter prior to the slit being opened. The air vents prevent buildup of positive pressure within the catheter adapter thereby permitting flashback of blood into the catheter and a forward chamber of the catheter adapter.

The septum actuator generally includes a plastic or metallic tubular body having a probing end and a contact end. The probing end is positioned adjacent to the pathway of the septum, and the contact end is positioned adjacent to a proximal opening of the catheter adapter. The probing end of the septum actuator is advanced against the septum when a probe is inserted into the proximal opening of the catheter adapter. As the probe contacts the contact surface of the septum actuator, the septum actuator is advanced in a distal direction thereby deforming or otherwise displacing the barrier surface of the septum and a distal direction. When in the stressed position, the slit or slits in the barrier surface assume an opened position thereby enabling free flow of fluid through the catheter assembly. Upon release of the septum actuator, the slit or slits in the barrier surface resume their closed position.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 4, shown in parts A and B, shows a cross-section side view of a catheter adapter, a septum actuator, and a septum in an activated and an inactivated configuration in accordance with a representative embodiment of the present invention.

FIG. 7 is a cross-section side view of the device of FIG. 5 following activation by a septum actuator in accordance with a representative embodiment of the present invention, following activation.

FIG. 8 is a cross-section perspective view of the device shown in FIG. 5, in accordance with a representative embodiment of the present invention.

FIG. 9, shown in parts A and B, shows a cross-section side view of a catheter adapter, a probe device, and a septum in an activated and an inactivated configuration in accordance with a representative embodiment of the present invention.

FIG. 10, shown in parts A-C, shows a cross-section side view of a catheter adapter, a septum actuator, and a septum in an activated and an inactivated configuration in accordance with a representative embodiment of the present invention.

FIG. 11, shown in parts A and B, shows a cross-section side view of a catheter adapter, a septum actuator, and a septum in an activated and an inactivated configuration in accordance with a representative embodiment of the present invention.

FIG. 15, shown in parts A and B, shows a cross-section side view of a catheter adapter, a septum actuator, and a septum in an activated and an inactivated configuration, wherein the septum includes a rigid collet leaf spring in accordance with a representative embodiment of the present invention.

FIG. 18, shown in parts A and B, shows a cross-section side view of a catheter adapter, a septum actuator, and a septum in an activated and an inactivated configuration, wherein the septum comprises a septum activation post in accordance with a representative embodiment of the present invention.

DETAILED DESCRIPTION OF THE INVENTION

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
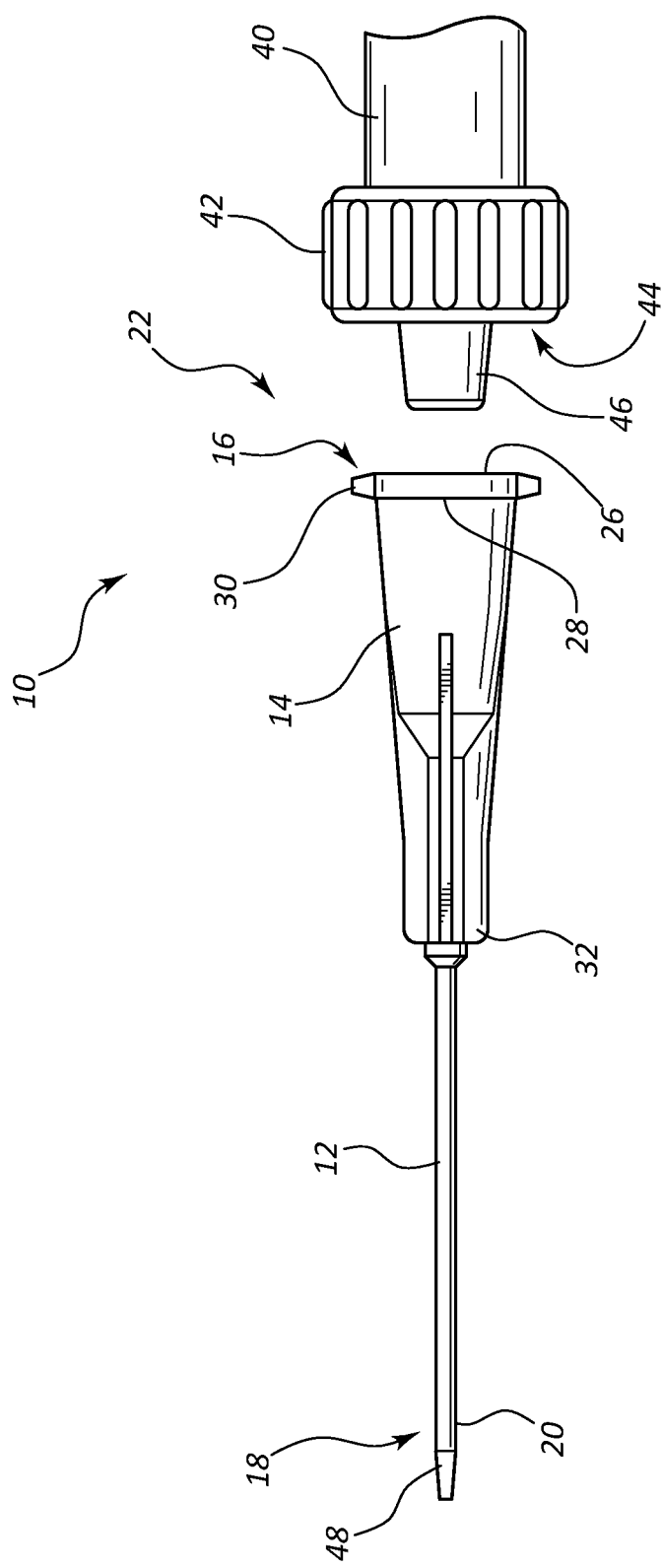
FIG. 1 is a perspective view of an embodiment of a catheter assembly in accordance with a representative embodiment of the present invention.

Referring now to FIG. 1, a catheter assembly 10 is illustrated. The catheter assembly 10 generally includes a catheter 12 coupled to a distal end 32 of a catheter adapter 14. The catheter 12 and the catheter adapter 14 are integrally coupled such that an internal lumen 16 of the catheter adapter 14 is in fluid communication with a lumen 18 of the catheter 12. The catheter 12 generally comprises a biocompatible material having sufficient rigidity to withstand pressures associated with insertion of the catheter into a patient. In some embodiments, the catheter 12 comprises a flexible or semi-flexible polymer material, such as silicone or polytetrafluoroethylene. Catheter 12 may further comprises a rigid metallic material, such as titanium, stainless steel, nickel, molybdenum, surgical steel, and alloys thereof.

One of skill in the art will appreciate that the features of the present invention may be incorporated for use with an over-the-needle catheter assembly. For example, one of skill in the art will appreciate that a flexible or semi-flexible polymer catheter may be used in combination with a rigid introducer needle to enable insertion of the catheter into a patient. One of skill in the art will further appreciate that surgically implanted catheters may also be used in combination with the present invention.

Once inserted into a patient, the catheter 12 and catheter adapter 14 provide a fluid conduit to facilitate delivery of a fluid to and/or retrieval of a fluid from a patient, as required by a desired infusion procedure. Thus, in some embodiments the material of the catheter 12 and the catheter adapter 14 are selected to be compatible with bio-fluids and medicaments commonly used in infusion procedures. Additionally, in some embodiments a portion of the catheter 12 and/or catheter adapter 14 is configured for use in conjunction with a section of intravenous tubing 40 to further facilitate delivery of a fluid to or removal of a fluid from a patient.

In some embodiments, a proximal end 22 of the catheter adapter 14 includes a flange 28. The flange 28 provides a positive surface which may be configured to enable coupling of an intravenous tubing or patient conduit 40 to the catheter assembly 10. In some embodiments, the flange 28 includes a set of threads 30. The threads 30 are generally provided and configured to compatibly receive a complementary set of threads 44 comprising a portion of a male luer or conduit coupler 42. The conduit coupler 42 is generally coupled to an end portion of the patient conduit 40 in a fluid-tight manner. In some embodiments, an inner portion of the conduit coupler 42 is extended outwardly to provide a probe surface 46.

The probe surface 46 is generally configured to compatibly insert within a proximal end 22 of the catheter adapter 14. Following insertion of the probe 46 into the proximal end 22 of the catheter adapter 14, the conduit coupler 42 is rotated to interlock the coupler 42 and the flange 28 (via the sets of threads 30 and 44). During the process of interlocking the coupler 42 and the flange 28, the probe surface 46 is advanced into the lumen 16 of the catheter adapter 14 to an inserted position. The inserted position of the probe surface 46 activates the catheter assembly 10 to enable flow of fluid through the catheter 12 and catheter adapter 14. Once the conduit coupler 42 and the catheter adapter 14 are attached, a fluid may be delivered to a patient via the patient conduit 40 and the inserted catheter 12.

Figure 2:
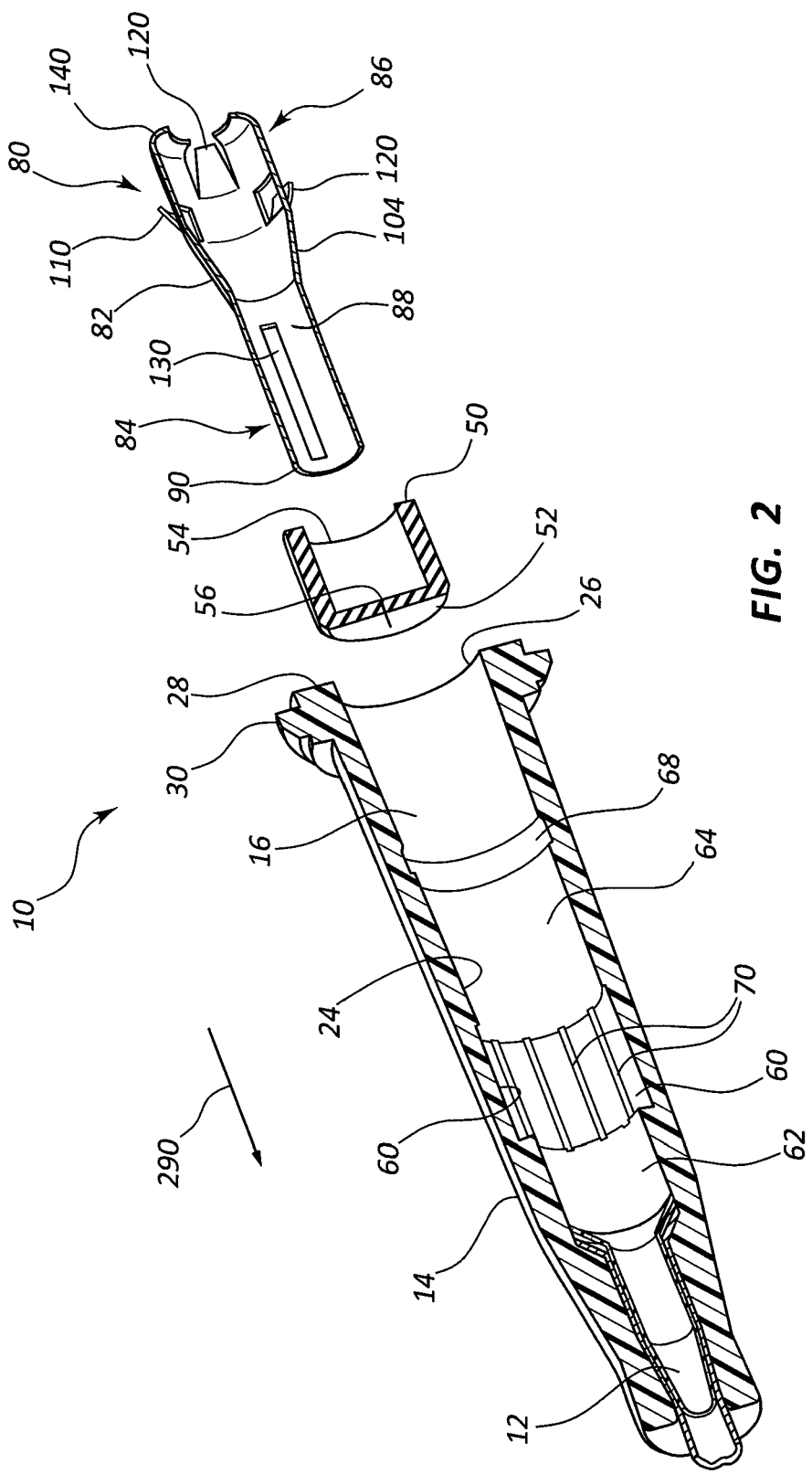
FIG. 2 is an exploded cross-sectioned view of a catheter assembly in accordance with a representative embodiment of the present invention.

Referring now to FIG. 2, an exploded, cross-sectional view of a catheter assembly 10 is shown. In some embodiments, the catheter adapter 14 includes various design features and components to control and/or limit flow of fluid through the catheter assembly 10. For example, in some embodiments of the present invention a septum valve or septum 50 is positioned within the inner lumen 16 of the catheter adapter 14. The septum 50 generally comprises a flexible, or semi-flexible polymer plug having an outer diameter that is configured to compatibly seat within a groove or channel 60 formed on an inner surface 24 of the catheter adapter 14. In some embodiments, the septum 50 is barrel or can shaped having a barrier surface 52 comprising a distal end of the septum 50 and further having an opening 54 comprising a proximal end of the septum 50. When positioned within the channel 60, barrier surface 52 of the septum 50 divides the inner lumen 16 of the catheter adapter 14 into a forward fluid chamber 62 and a rearward fluid chamber 64. Thus, the presence of the septum 50 controls or limits passage of fluid between the forward and rearward fluid chambers 62 and 64. Specifically, a chosen configuration of the barrier surface 52 of the septum 50 largely determines the ability of a fluid to flow through the inner lumen 16 of the catheter adapter 14.

For example, in some embodiments the barrier surface 52 of the septum 50 is configured to include a slit 56. The slit 56 is configured to provide selective access or flow of a fluid through the barrier surface 52. In some embodiments, the slit 56 is configured to remain in a closed, fluid-tight position until activated or stressed into an opened configuration by advancing a septum actuator 80 against barrier surface 52 in a distal direction 290. In some embodiments, slit 56 is configured to permit the passage of an introducer needle or other probing device to assist in catheterization or subsequent treatment of the patient. In some embodiments, the barrier surface 52 comprises one slit 56. In other embodiments, the barrier surface 52 plurality of slits.

In general, slit 56 forms a fluid tight seal prior to being actuated by septum actuator 80. However, for some infusion therapy techniques, it may be desirable to permit a controlled flow of fluid through the septum 50 prior to activating the septum 50 with the septum actuator 80. Thus, in some embodiments slit 56 does not form a fluid tight seal. Rather, slit 56 forms a leak orifice to permit controlled flow of liquid or air between the forward and rearward chambers 62 and 64 (not shown).

The groove or channel 60 into which the septum is seated comprises a recessed portion of the inner surface 24 of the catheter adapter 14. The outer diameter of the septum 50 is generally configured to compatibly and securely seat within the channel 60. For example, in some embodiments the outer diameter of the septum 50 is selected to be both slightly smaller than the diameter of the channel 60 and slightly larger than the diameter of the inner lumen 16. As such, the septum 50 is retained within the channel 60 during use of the catheter assembly 10.

For some infusion therapy techniques, air flow between the forward and rearward chambers 62 and 64 may be desirable. For example, for those embodiments comprising a septum 50 having a fluid-tight slit 56 and 66, passage of air from the forward chamber 62 to the rearward chamber 64 is prohibited prior to opening or actuating septum 50 via septum actuator 80, as previously discussed. Thus, when the catheter 12 of the catheter assembly 10 is inserted into the vascular system of a patient, a positive pressure develops within the forward chamber 62 thereby preventing a desired flashback of the patient's blood into the catheter adapter 14. An observable flashback is generally desirable to confirm accurate placement of the catheter tip 20 within the vein of the patient. Thus, some embodiments of the present invention include features or elements to enable airflow between the forward chamber 62 and the rearward chamber 64, without requiring activation of the septum 50 with the septum actuator 80. As such, some embodiments of the present invention provide an observable flashback, as generally desired for infusion procedures.

For example, in some embodiments slit 56 is modified so as to permit controlled leakage of air or liquid, as previously discussed. In other embodiments, a plurality of air vent channels 70 is interposed between the septum 50 and the inner surface 24 of the catheter adapter 14. The air vent channels 70 relieve the positive pressure within the forward chamber 62 by providing an access for air to bypass the septum 50 into the rearward chamber 64. In some embodiments, the air vent channels 70 are constructed by removing portions of the channel 60 surface, resulting in a plurality of generally parallel grooves. In other embodiments, an outer surface of septum 50 is modified to include a plurality of generally parallel grooves (not shown), as shown and taught in U.S. patent application Ser. No. 12/544,625, which is incorporated herein by reference.

With continued reference to FIG. 2, the septum actuator 80 comprises a probe-like structure that is primarily housed in the rearward chamber 64 of the catheter adapter 14. Septum actuator 80 generally comprises a tubular body 82 having a distal end 84 and a proximal end 86. The tubular body 82 comprises a rigid or semi-rigid material, such as a plastic or metallic material. The tubular body 82 further comprises an inner lumen 88 for facilitating flow of a fluid and/or liquid through the septum actuator 80. Septum actuator 80 may further include various features 110, 120 and 130 to retain septum actuator 80 within catheter adapter 14, and to optimize fluid flow through and around septum actuator 80.

The distal end 84 of the tubular body 82 is configured to compatibly abut and thereby deform barrier surface 52 of septum 50. Distal end 84 is generally configured to compatibly insert within opening 54 of septum 50. The distal end 84 further includes a probing surface 90 which extends through the opening 54 of the septum 50 to a position proximal to the barrier surface 52 of the septum 50. The probing surface 90 is advanced against barrier surface 52 as septum actuator 80 is advanced through the catheter adapter 14 in distal direction 290.

Figure 3A:
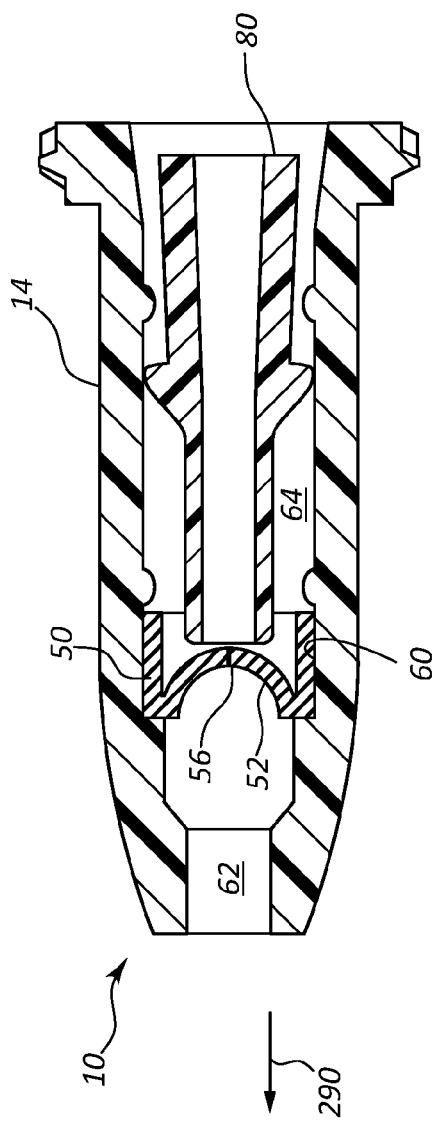
FIG. 3, shown in parts A and B, shows a cross-section side view of a catheter adapter, a septum actuator, and a septum in an activated and an inactivated configuration in accordance with a representative embodiment of the present invention.
Figure 3B:
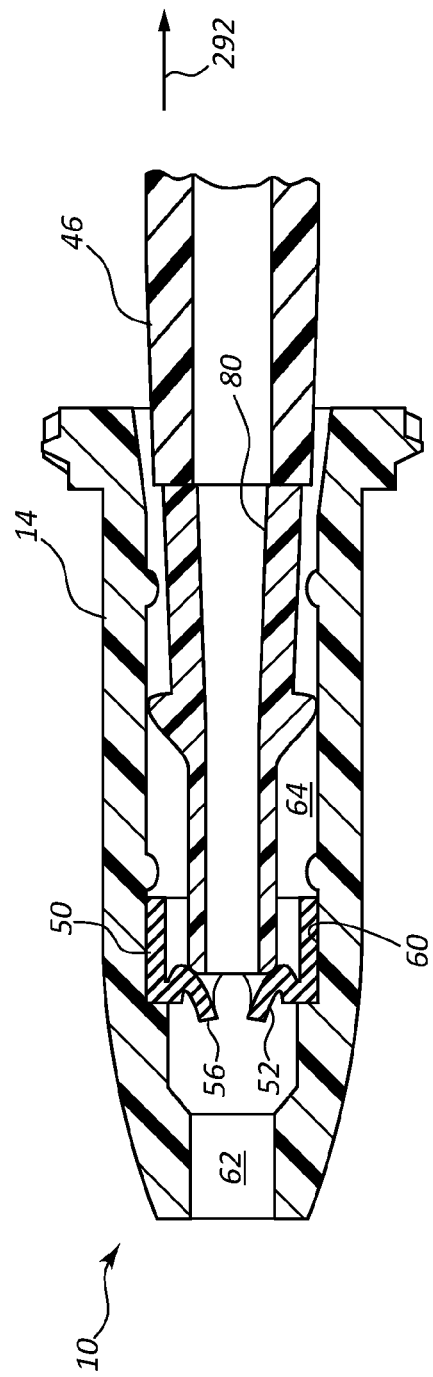

Referring now to FIGS. 3A and 3B, a bistable septum 50 is shown having a concave barrier surface 52. Prior to activation, septum 50 forms a fluid tight seal at slit 56. As septum actuator 80 is advanced in distal direction 290, barrier surface 52 is stressed or biased into an open position, as shown in FIG. 3B. When probe 46 is removed from catheter adapter 14, the resilient nature of septum 50 biases septum actuator 80 in a proximal direction 292 such that a fluid tight seal is once again formed at slit 56, as shown in FIG. 3A.

In some embodiments, the septum actuator and septum are integrated into a single flexi-plunger unit, as shown in FIGS.

4A and B. For this embodiment, septum 50 comprises a disk shaped member having a center portion to which is attached a shaft portion of actuator 80. Prior to activation, septum 50 forms a fluid tight seal around its perimeter surface against the inner surface of catheter adapter 14. In some embodiments, septum 50 further comprises a plurality of micro-vents to allow air leakage but not fluid leakage. Thus, the present embodiment provides for multiple accesses with a means of cannula compatibility and air venting.

In some embodiments the inner surface of catheter adapter 14 further comprises a plurality of grooves such that as septum 50 is biased in distal direction 290, the perimeter surface of septum 50 overlaps grooves 78 thereby disrupting the fluid tight seal around its perimeter surface, as shown in FIG. 4B. Thus, fluid is permitted to pass through a vent portion of actuator 80 and pass into forward fluid chamber 62 via grooves 78. When probe 46 is removed from catheter adapter 14, the resilient nature of septum 50 biases septum actuator in proximal direction 292 such that a fluid tight seal is once again established around the perimeter of septum 50, as shown in FIG. 4A.

Figure 5:
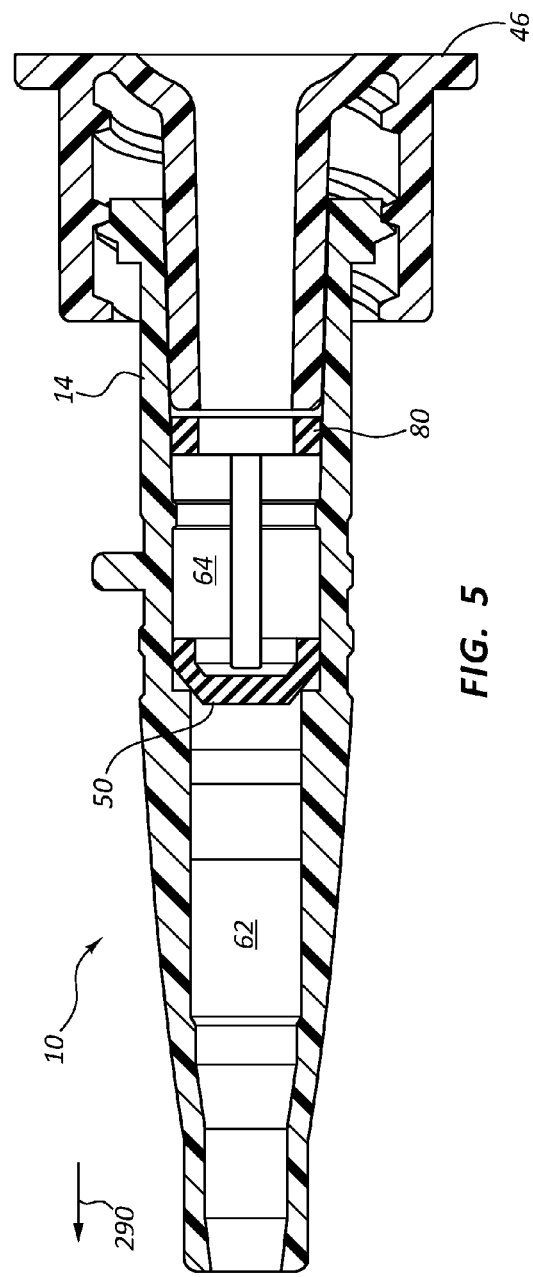
FIG. 5 is a cross-section side view of a catheter adapter and an integrated plunger and septum in accordance with a representative embodiment of the present invention, prior to activation.
Figure 6:
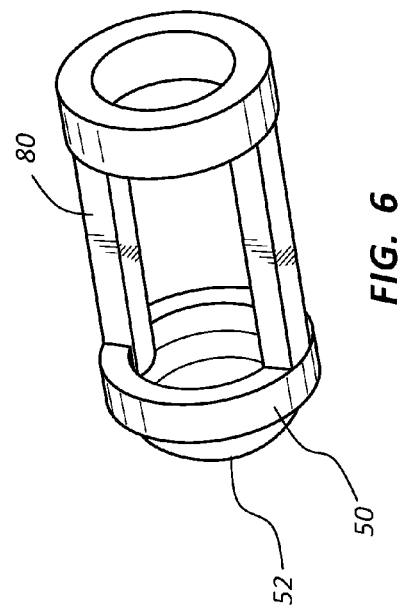
FIG. 6 is a perspective view of an integrated plunger and septum in accordance with a representative embodiment of the present invention, following activation.

Referring now to FIGS. 5-8, another embodiment of an integrated septum and septum actuator is shown. In some embodiments an integrated septum and septum actuator is provided wherein the septum actuator 80 comprises a rigid plastic pusher having a ring shaped base and extension arms which are coupled to a dome or disk shaped septum 50. The integrated septum and septum actuator are positioned within the catheter adapter 14 such that septum 50 is immobilized and septum actuator 80 is capable of moving a proximal and distal direction. Septum 50 further comprises a plurality of microvents that open when the septum is biased in a distal direction 290 by septum actuator 80. Septum actuator 80 is biased in distal direction 290 as probe 46 is threaded onto catheter adapter 14, as shown in FIG. 7. When probe 46 is unthreaded from catheter adapter 14, the resilient or restorative nature of septum 50 biases septum actuator 80 in proximal direction 292 thereby closing the septum microvents, as shown in FIGS. 5 and 8.

Referring now to FIGS. 9A and 9B, in some embodiments septum 50 comprises a convex barrier surface 52. Prior to activation, septum 50 forms a fluid tight seal at slit 56. As probe device 46 is advanced in distal direction 290, barrier surface 52 is biased into an open position, as shown in FIG. 9B. When probe 46 is removed from catheter adapter 14, the resilient nature of septum 50 resumes its fluid tight seal at slit 56, as shown in FIG. 9A.

In some embodiments, catheter assembly 10 further comprises a disruption cone 66. Referring now to FIGS. 10A-10C, disruption cone 66 is provided as a rigid barrier over which septum 50 is biased by septum actuator 80. Prior to activation, an exterior perimeter of septum 50 forms a fluid tight seal with the inner surface of catheter adapter 14. As probe device 46 is advanced in distal direction 290, septum actuator 80 contacts septum 50, thereby biasing septum 50 over disruption cone 66, as shown in FIG. 10B. When biased, the fluid tight seal of septum 50 is disrupted thereby permitting passage of fluid between septum 50 in the inner surface of catheter adapter 14. Channels formed in septum actuator 80 and disruption cone 66 further permit passage of fluid through catheter adapter 14. When probe 46 is removed from catheter adapter 14, the resilient nature of septum 50 biases septum actuator 80 in a proximal direction 292 such that a fluid tight seal is once again formed between septum 50 and catheter adapter 14, as shown in FIG. 10A.

Referring now to FIGS. 11A and 11B, in some embodiments septum 50 and septum actuator 80 are configured such that actuator 80 is not allowed to completely penetrate septum 50. In some embodiments, this is due to the shortened catheter adapter space in which septum actuator 80 is permitted to translate within. In other embodiments, the length of barrier surface 52 is such that when septum actuator 80 penetrates septum 50, barrier surface 52 contacts wedge 94 of catheter adapter 14 thereby flexing and slightly deforming barrier surface 52. When this occurs, the distal end of septum actuator 80 is mechanically prevented from bypassing the narrow diameter caused by the interaction between wedge 94 and barrier surface 52. As such, the resilient, restorative nature and geometric configuration of septum 50 biases septum actuator 80 in proximal direction 292 following removal of probe 46 from catheter adapter 14, as shown in FIG. 11A.

Figure 12:
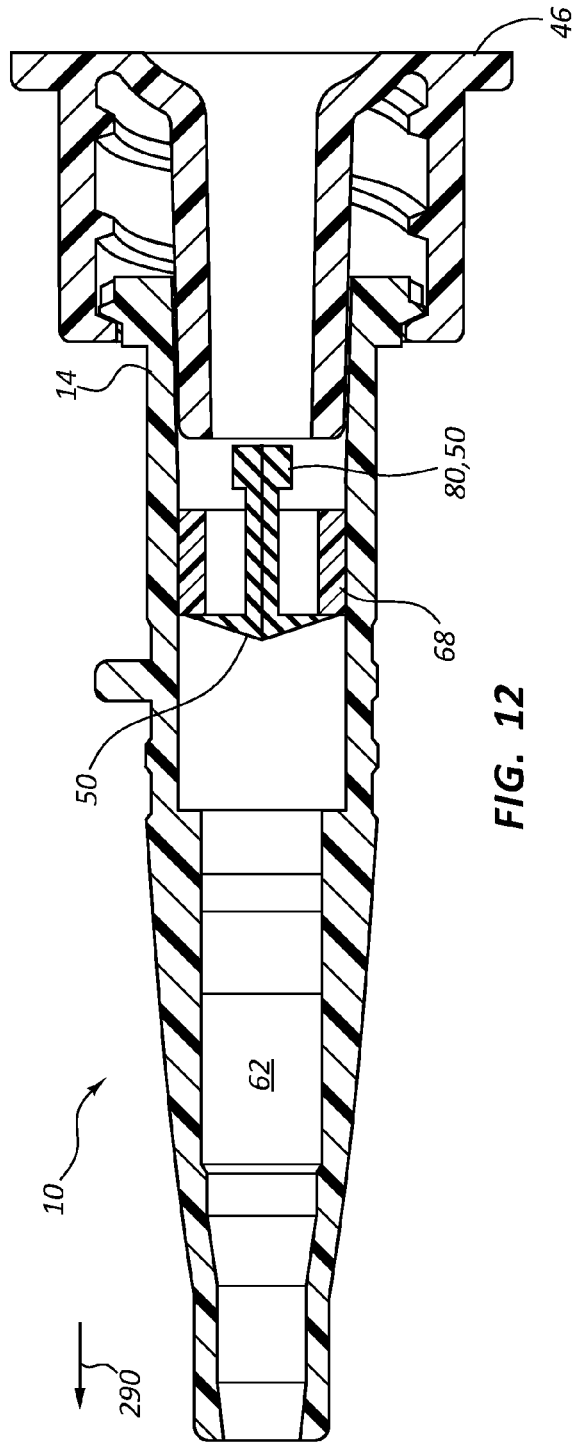
FIG. 12 is a cross-section side view of a catheter adapter, a septum actuator, and an integrated actuator and restraining collar in accordance with a representative embodiment of the present invention, prior to activation.
Figure 13:
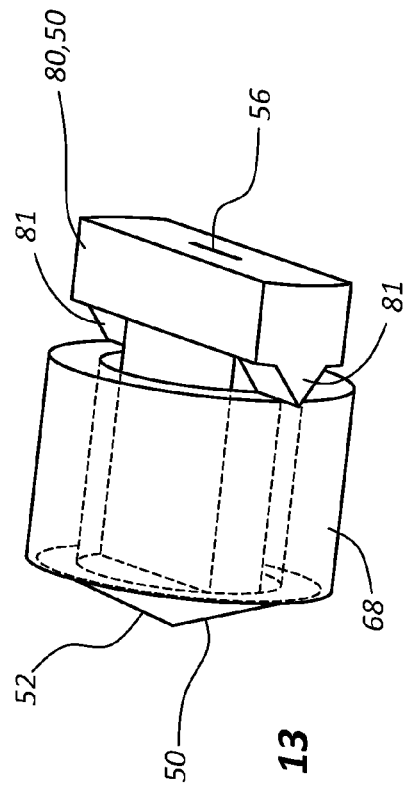
FIG. 13 is a perspective view of an integrated actuator and restraining collar in accordance with a representative embodiment of the present invention.
Figure 14:
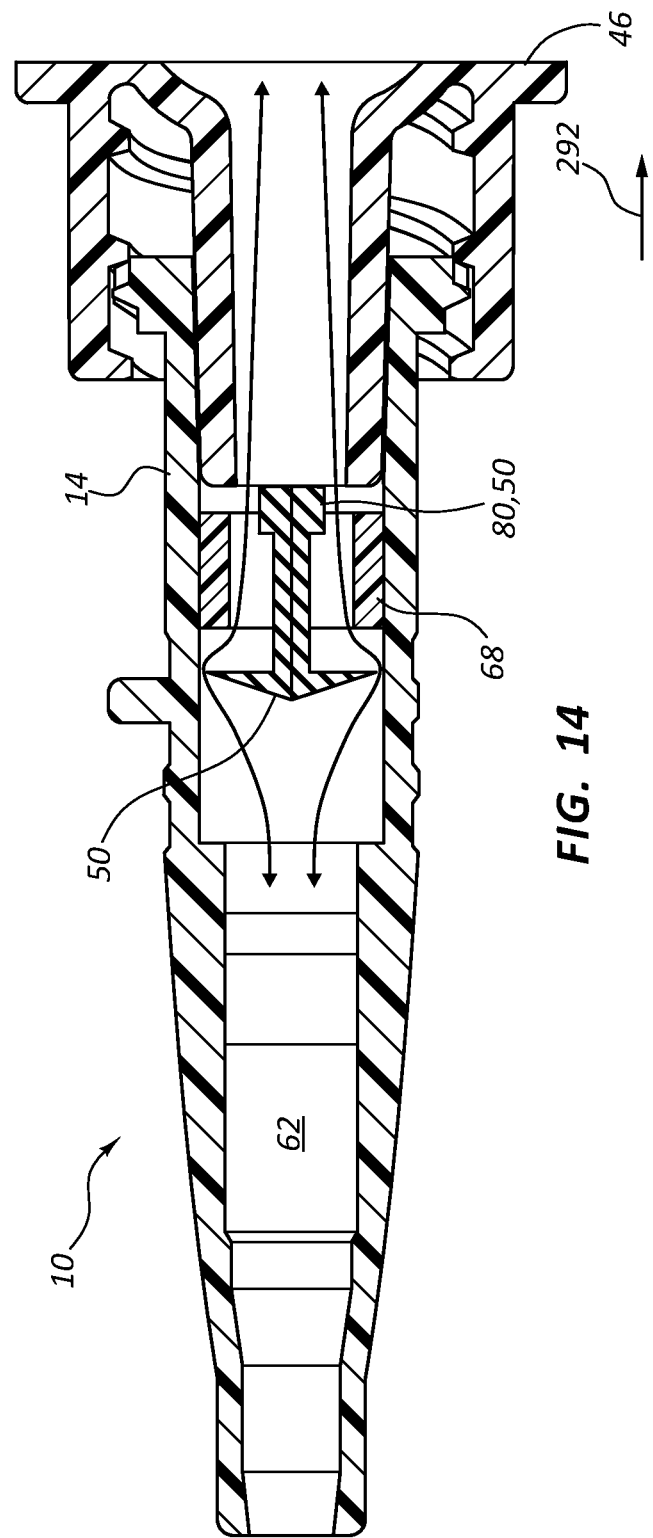
FIG. 14 is a perspective side view of the device shown in FIG. 12, following activation.

Referring now to FIGS. 12-14, in some embodiments septum actuator 80 and septum 50 comprise an integrated, elastomeric unit. In particular, in some embodiments catheter adapter 14 is configured to house a restraining collar 68 which includes an outer surface that forms a fluid tight seal with the inner surface of catheter adapter 14, and further includes a center pathway through which septum actuator/septum 80, 50 is retained. The septum actuator portion of the integrated device further comprises a spring feature 81 that creates tension across the integrated device thereby pulling the septum portion 50 of the integrated device against the distal surface a restraining collar 68 to form a fluid tight seal, as shown in FIGS. 12 and 13. Upon insertion of a probe device 46 into catheter adapter 14, the probe device contacts the septum actuator portion 80 of the integrated device thereby temporarily defeating spring features 81 in disrupting the seal between the septum portion 50 of the integrated device and restraining collar 68, as shown in FIG. 14. Fluid is then permitted to flow through the center pathway of restraining collar 68 and bypass the septum portion 50 of the integrated device. When probe 46 is removed from catheter adapter 14, the resilient nature of spring features 81 biased the integrated device in proximal direction 292, thereby reestablishing the fluid tight seal between septum portion 50 and restraining collar 68.

Referring now to FIGS. 15A and 15B, in some embodiments septum 50 further comprises a rigid collet leaf spring 76 which is located internally within septum 50. Catheter adapter 14 further comprises a rigid, bored out spike 74 which prevents the distal end of septum 50 from collapsing during activation of the septum. Collet leaf springs 76 are provided as a rigid element for compressing the distal end of septum 50 when septum 50 is compressed by probe device 46, as shown in FIG. 15B. Collet leaf springs 76 further provide a rigid structure over which barrier surface 52 is biased into an opened position. When probe 46 is removed from catheter adapter 14, the resilient nature of septum 50, and in particular the distal end of septum 50, biases the proximal portion of septum 50 and collet leaf spring 76 in proximal direction 292, such that a fluid tight seal is once again formed at slit 56, as shown in FIG. 15A.

Figure 16:
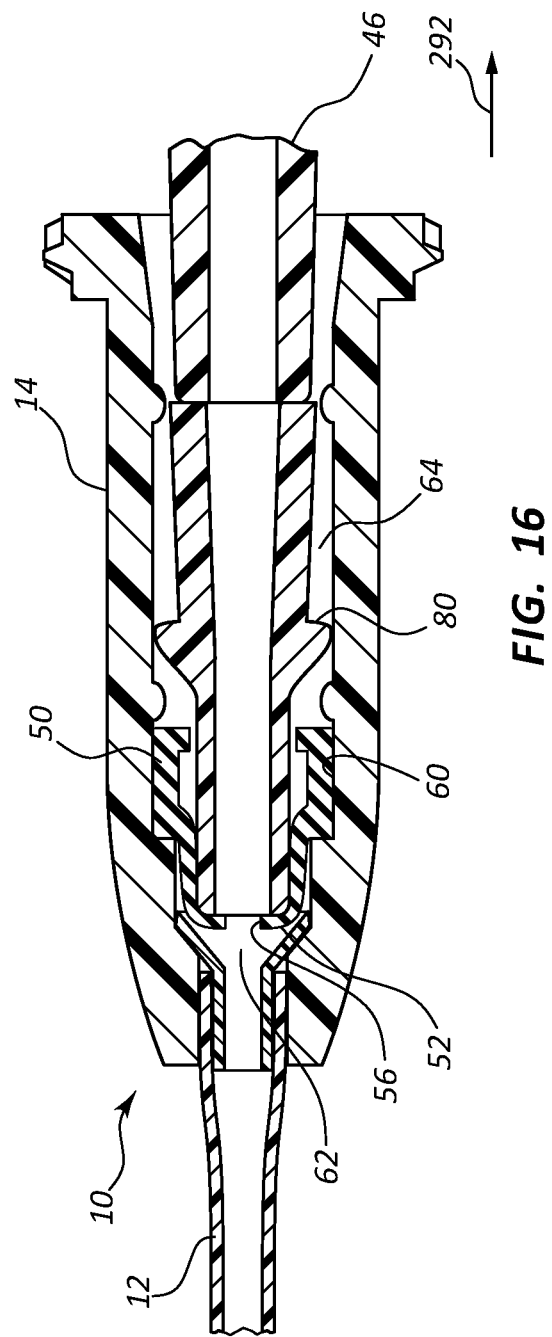
FIG. 16 is a cross-section side view of a catheter adapter, a septum actuator, and a septum in an activated configuration, wherein the septum slit is minimized in accordance with a representative embodiment of the present invention.

Referring now to FIG. 16, in some embodiments septum slit 56 is undersized such that septum actuator 80 is prevented from fully penetrating slit 56. As such, when probe device 46 is removed from catheter adapter 14, the resilient nature of septum 50, due to the undersized septum slit 56, biases septum actuator 80 in proximal direction 292 such that a fluid tight seal is once again formed at slit 56. In other words, the septum is slit small so that the silicone or other material of septum 50 will exert a returning or restoring force moving actuator 80 back to its initial state in the sealing off fluid flow through catheter adapter 14.

Figure 17A:
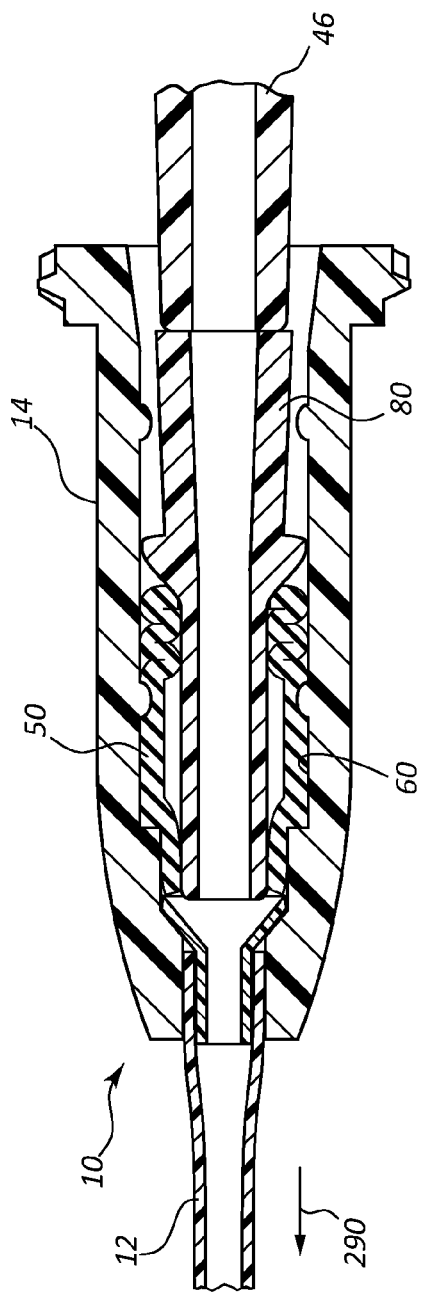
FIG. 17, shown in parts A and B, shows a cross-section side view of a catheter adapter, a septum actuator, and a septum in an activated and an inactivated configuration in accordance with a representative embodiment of the present invention.
Figure 17B:
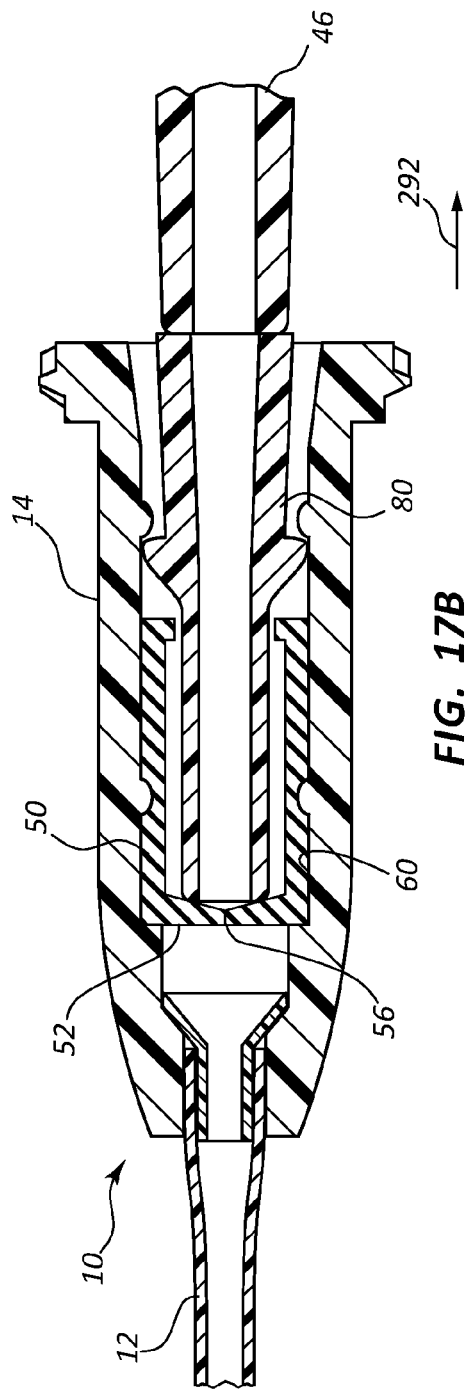

With reference to FIGS. 17A and 17B, a rear flange of septum 50 is elongated such that prior to activation of septum 50, the rear flange is positioned in proximity to a rigid opposing surface of septum actuator 80. As septum actuator is advanced in distal direction 290, the rear flange is compressed between septum actuator 80 and an internal feature of catheter adapter 14. Following removal of a probe device 46 from catheter adapter 14, the resilient nature of the rear flange of septum 50 biases septum actuator 80 in proximal direction 292 such that a fluid tight seal is once again formed at slit 56, as shown in FIG. 17B.

In other embodiments, septum 50 comprises an integrated septum actuator, shown as septum activation post 98. Activation post 98 is positioned such that when probe device 46 is inserted into catheter adapter 14, probe device 46 contacts activation post 98 thereby biasing a portion of barrier surface 52 in a distal direction 290, thereby opening slit 56, as shown in FIG. 18B. Upon removal of probe 46 from catheter adapter 14, the resilient nature of barrier surface 52 biases activation post 98 and barrier surface 52 to its original closed and sealed orientation, as shown in FIG. 18A.

Figure 19B:
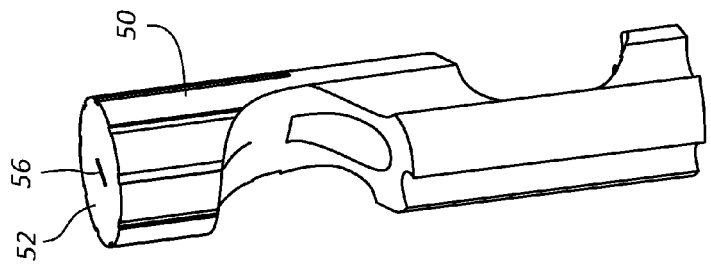
FIG. 19, shown in parts A-C, shows a catheter adapter, a septum, in a septum actuator in an activated and an inactivated configuration in accordance with a representative embodiment of the present invention.
Figure 19A:
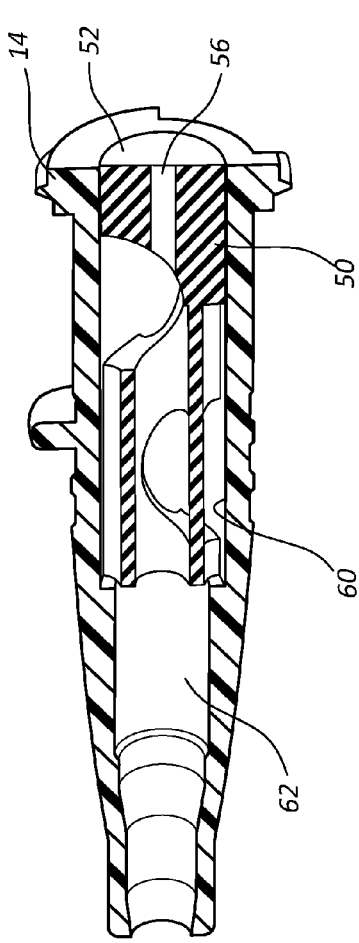
Figure 19C:
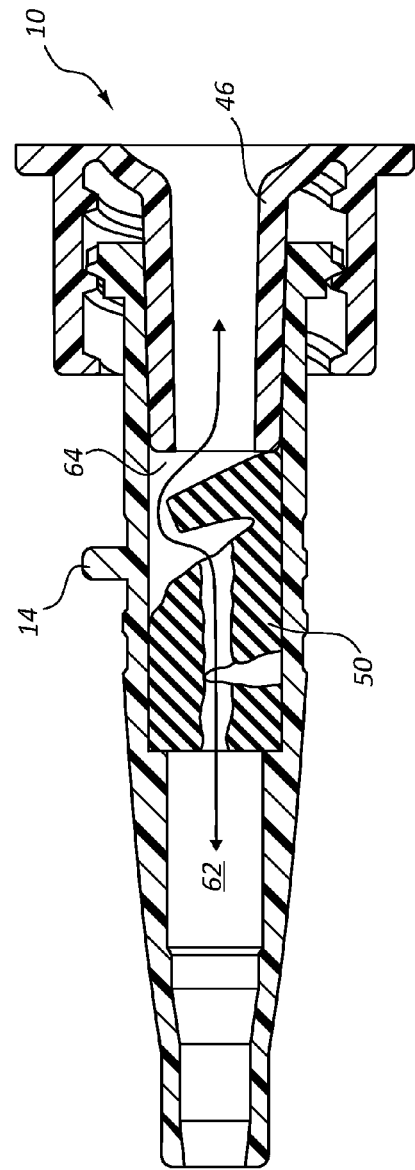

In some embodiments, septum 50 comprises a collapsible septum, as shown in FIGS. 19A-19C. In particular some embodiments comprise an elastomeric septum that is designed with a pre-pierced slit 56 down its length to allow for cannula insertion and retention until such time that the cannula is placed in the vein and removed. Microvents near the sealing surface allow for air venting but no liquid leakage. Upon probe device 46 engagement, several cutout areas allow the septum cylinder to collapse on itself thereby allowing for an opening of a liquid fluid path through catheter adapter 14. Upon removal of probe device 46, the natural elastomeric properties of septum 50 force the septum back into his resting, relaxed state and sealed the fluid path. One advantage of this embodiment is that the actuating piece, or septum actuator, and the septum comprise a single, integrated component. The present embodiment may further allow for a smooth cleaning surface at the proximal opening of catheter adapter 14.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An integrated septum and septum actuator comprising a base having a fluid pathway and an extension arm extending outwardly from the base, the extension arm being coupled to a septum, the septum being deformable from a relaxed position to a stressed position, wherein the stressed position biases the septum to provide a pathway around an outer surface of the septum.

2. The integrated septum and septum actuator of claim 1, wherein the septum further comprises a plurality of microvents that open when the septum is in the stressed position.

3. The integrated septum and septum actuator of claim 1, further comprising a plurality of extension arms.

4. The integrated septum and septum actuator of claim 1, wherein the septum is at least one or dome shaped and disk shaped.

5. The integrated septum and septum actuator of claim 1, wherein the septum is mechanically deformed from the relaxed position to the stressed position.

6. The integrated septum and septum actuator of claim 2, wherein the relaxed position closes the pathway around the outer surface of the septum and closes the plurality of microvents.

7. The integrated septum and septum actuator of claim 1, wherein the septum comprises an elastic material.

8. The integrated septum and septum actuator of claim 1, wherein the septum is resilient.

9. A system for controlling fluid flow in a catheter assembly, comprising:
   an intravenous catheter assembly having a catheter adapter comprising an inner lumen;
   an integrated septum and septum actuator disposed within a portion of the inner lumen, the integrated septum and septum actuator comprises a base having a fluid pathway and an extension arm extending outwardly from the base, the extension arm being coupled to a septum being deformable from a relaxed position to a stressed position, wherein a pathway around an outer surface of the septum is closed when the septum is in the relaxed position, and the pathway around the outer surface of the septum is open when the septum is in the stressed position.

10. The system of claim 9, wherein the septum further comprises a plurality of microvents that open when the septum is in the stressed position, and wherein a proximal end of the base is accessed by inserting an external device into a proximal opening of the catheter adapter.

11. The system of claim 10, further comprising a lumen forming the fluid pathway through the base and the extension arm.

12. The system of claim 9, further comprising a ventilation channel interposed between the septum and an inner surface of the inner lumen of the catheter adapter, the ventilation channel having a surface area and a perimeter selected to permit passage of at least one of air and blood at a desired rate of flow.

13. The system of claim 10, wherein a distal end of the extension arm is fixedly attached to a proximal surface of the septum.

14. The system of claim 10, wherein the integrated septum and septum actuator is slidably housed within a portion of the inner lumen and is capable of moving between a proximal position and a distal position, wherein when the integrated septum and septum actuator is in the proximal position the septum is in the relaxed position, and wherein when the integrated septum and septum actuator is in the distal position, the distal end of the extension arm biases the septum into the stressed position.

15. A method for manufacturing a catheter assembly having features for controlling fluid flow within the catheter assembly, the method comprising:
   providing an integrated septum and septum actuator device comprising a base having a fluid pathway and an extension arm extending outwardly from the base, the extension arm being coupled to a septum being deformable from a relaxed position to a stressed position, wherein the stressed position biases the septum to provide a pathway around an outer surface of the septum;
   providing an intravenous catheter assembly having a catheter adapter comprising an inner lumen; and
   disposing the integrated septum and septum actuator within a portion of the inner lumen of the catheter adapter.

16. The method of claim 15, further comprising disposing the integrated septum and septum actuator within a portion of the inner lumen adjacent to a proximal opening of the catheter adapter, wherein a proximal end of the base is accessed by inserting an external device into the proximal opening of the catheter adapter.

17. The method of claim 15, further comprising a plurality of extension arms.

18. The method of claim 15, further comprising fixedly attaching a distal end of the extension arm to a proximal surface of the septum.

19. The method of claim 15, further comprising a step for providing the septum with a plurality of microvents that are closed when the septum is in the relaxed position, and are opened when the septum is in the stressed position.

20. The system of claim 9, further comprising a plurality of extension arms.

* * * * *